United States Patent [19]

Helland

[11] Patent Number: 5,571,163
[45] Date of Patent: Nov. 5, 1996

[54] COMBINATION PACING AND DEFIBRILLATING LEAD HAVING ATRIAL SENSING CAPABILITY AND METHOD

[75] Inventor: John R. Helland, Redmond, Wash.

[73] Assignee: Pacesetter, Inc., Sylmar, Calif.

[21] Appl. No.: 401,846

[22] Filed: Mar. 10, 1995

Related U.S. Application Data

[63] Continuation-in-part of Ser. No. 125,448, Sep. 22, 1993, Pat. No. 5,431,681.

[51] Int. Cl.[6] ................................................ A61B 5/04
[52] U.S. Cl. ............................................................ 607/123
[58] Field of Search ................................. 607/122, 123

[56] References Cited

U.S. PATENT DOCUMENTS

| | | | |
|---|---|---|---|
| 4,402,329 | 9/1983 | Williams | 607/123 |
| 4,932,407 | 6/1990 | Williams | 607/122 |
| 5,269,319 | 12/1993 | Schulte et al. | 607/123 |
| 5,330,522 | 7/1994 | Kreyenhagen | 607/122 |
| 5,456,706 | 10/1995 | Pless et al. | 607/122 |

Primary Examiner—William E. Kamm
Assistant Examiner—Scott M. Getzow
Attorney, Agent, or Firm—Harold C. Schloss

[57] ABSTRACT

A combination lead for use with an implanted pulse generator which may be a pacemaker or defibrillator or combination thereof. The lead can deliver an electrical charge to pace, cardiovert or defibrillate the ventricles of the heart, and can sense cardiac activity in the heart. The lead includes atrial ring sensors capable of sensing electrical activity in the atrial cavity. The lead allows cardioversion and/or defibrillation stimuli to be provided by a large surface area electrode which is passively implanted in the ventricle, and allows the pulse generator to provide ventricular pacing appropriately synchronized to atrial depolarizations, cardioversion or defibrillation.

42 Claims, 5 Drawing Sheets

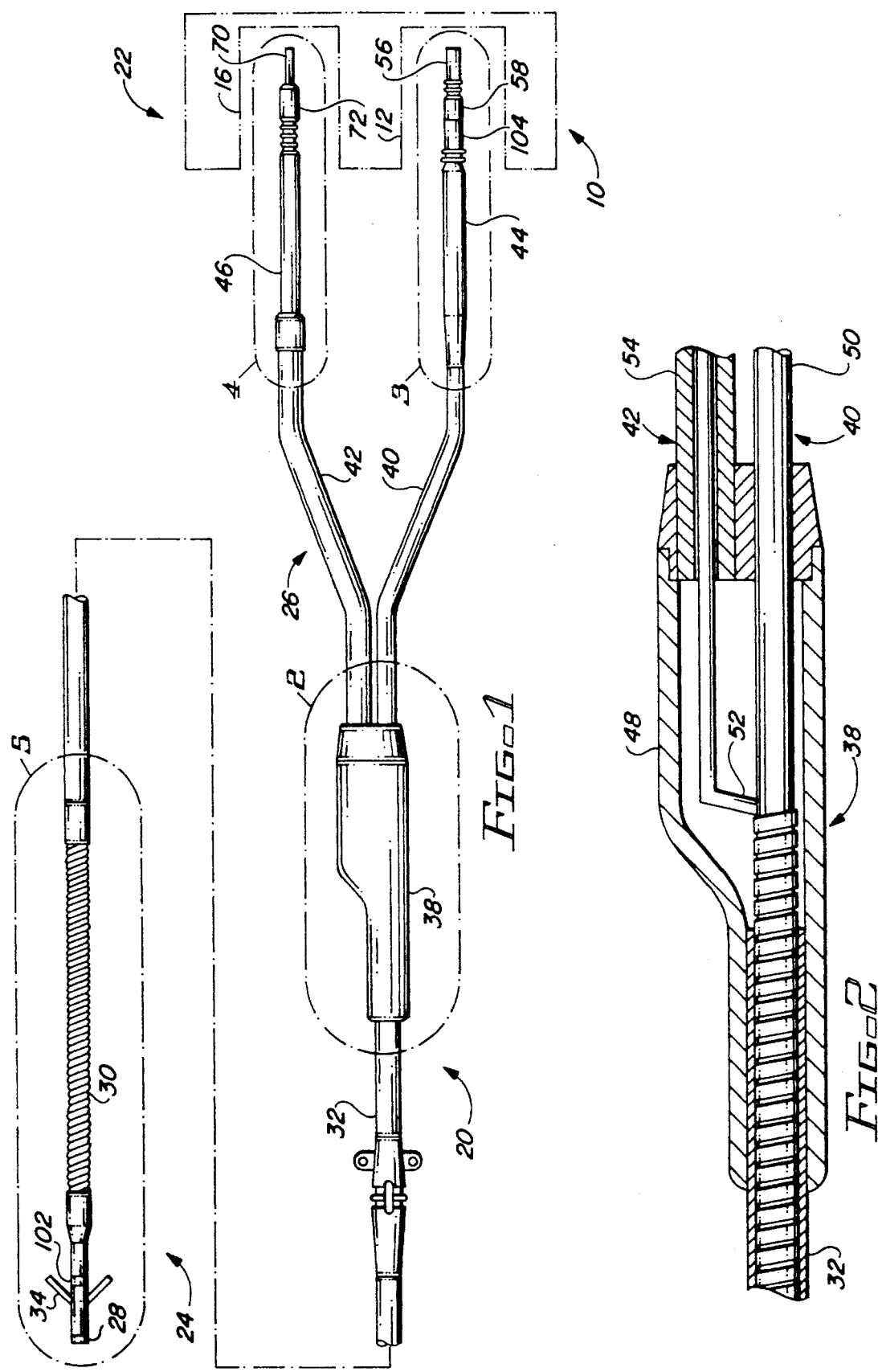

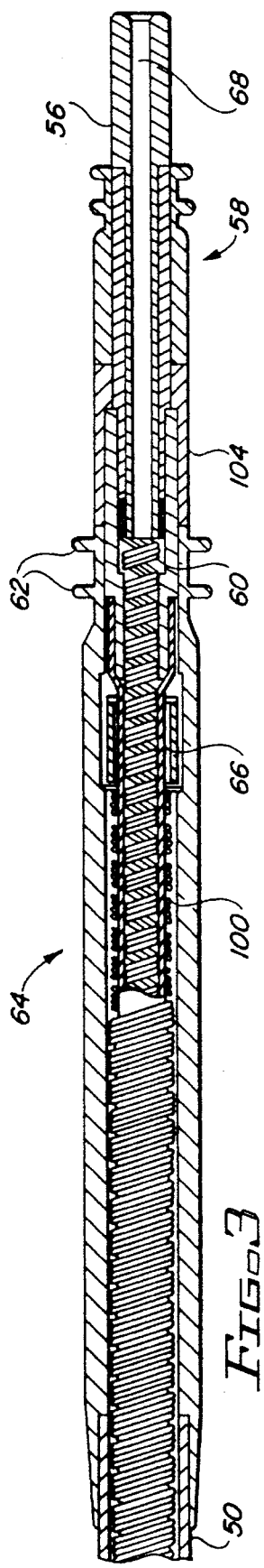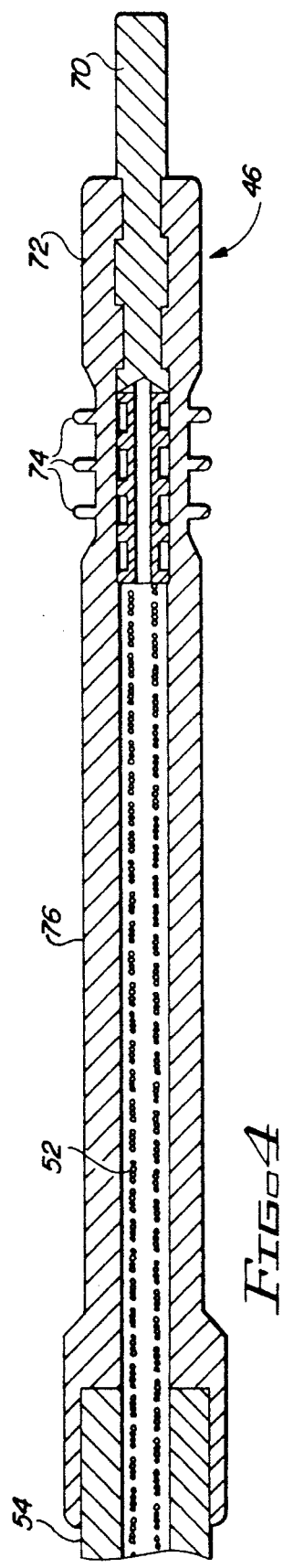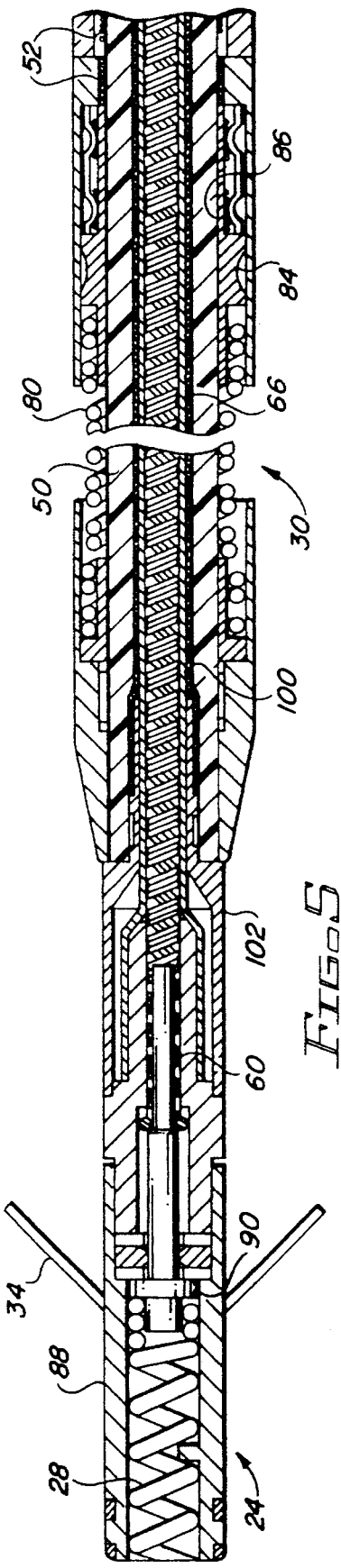

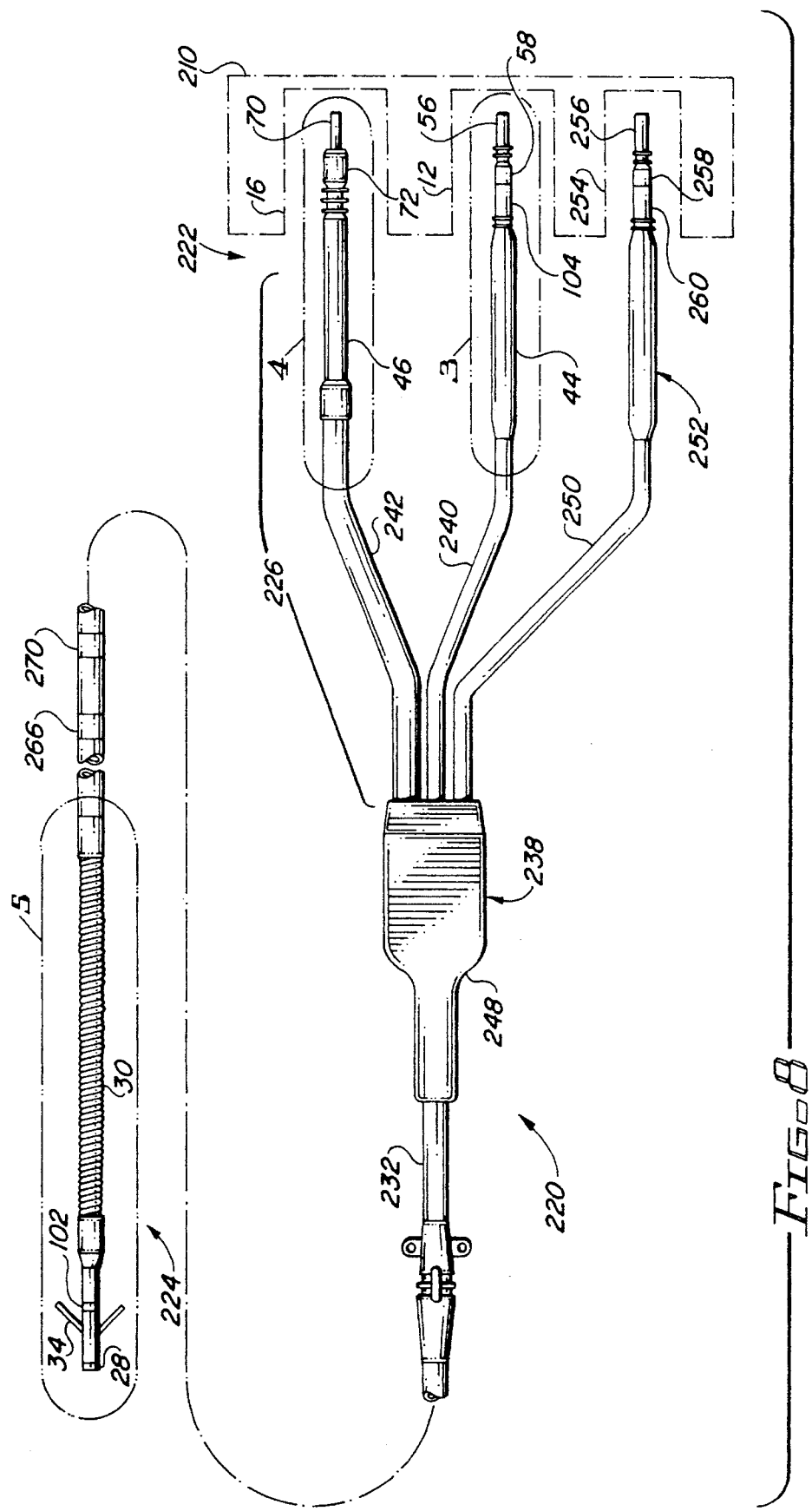

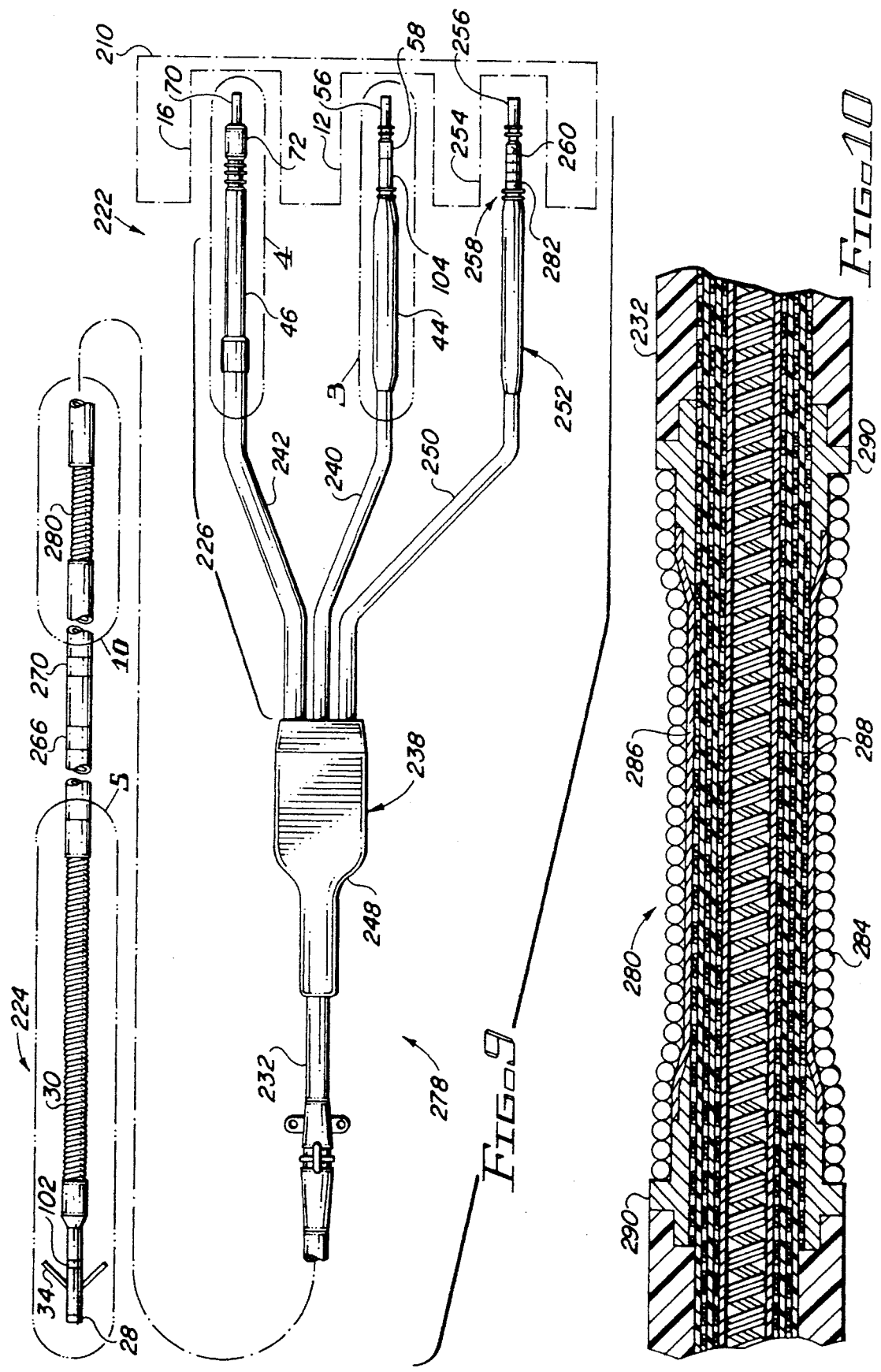

COMBINATION PACING AND DEFIBRILLATING LEAD HAVING ATRIAL SENSING CAPABILITY AND METHOD

This is a continuation-in-part of U.S. patent application Ser. No. 08/125,448 filed on Sep. 22, 1993, now U.S. Pat. No. 5,431,681.

FIELD OF THE INVENTION

The present invention relates generally to medical electronic devices and, more particularly, to implantable devices for pacing, cardioverting or defibrillating a heart. Specifically, the present invention is directed to a lead designed to be placed through the right atrium into the right ventricle which can pace, cardiovert or defibrillate the heart, and sense cardiac activity in the right atrium or the right ventricle of the heart, in conjunction with an implanted defibrillator.

BACKGROUND OF THE INVENTION

A number of types of implantable devices are in use to monitor and control the electrical activity of the heart. For example, it is known to have an implanted pacemaker interconnected via a transvenous pacing lead to an electrode in intimate contact with the myocardial tissue of the heart. The electrode can both sense the electrical activity of the heart and deliver an electrical stimulus provided by the pacemaker when required. Other systems include pacemakers and transvenous pacing leads which have a variety of sensor electrodes proximally spaced behind the tip electrode of the pacing lead. The sensors provide information to the pacemaker.

There are also systems which monitor and provide automatic defibrillation utilizing an implanted power source and an electrode system, either attached to the surface of, or implanted within, the heart. Still other systems combine the pacemaker function with an automatic defibrillation capability, and may include multiple leads extending to internal as well as external portions of the heart.

Combination pacing and defibrillation systems having a combination pacing and sensing lead implanted into the ventricle, and a large surface area patch electrode affixed to or near the exterior surface of the heart, both of which are connected to a pacemaker and/or a defibrillator are also in use. Additionally, pacing systems may include a transvenously implanted lead which provides pacing and sensing only within the atrium. With this type of system, there may be two different pacing or sensor leads extending intravenously into the interior of the heart, in addition to a patch lead and electrode affixed to or near the epicardial surface of the heart, all connected to the pacemaker and/or defibrillator. During the implantation procedure, the attending physician may implant a combination lead having pacing and sensing electrodes, which also includes a defibrillation electrode mounted just proximally of the distal tip in the ventricle, and then test whether the defibrillation electrode can provide sufficient energy to defibrillate the heart to terminate ventricular fibrillation. In the event that defibrillation requires too much energy or cannot be accomplished by the combination lead, a second lead having a patch electrode to be affixed to or near the epicardial surface of the heart or nearby, such as in a subcutaneous or subcostal site, may be required. If such a patch electrode is also required, following affixation of the patch electrode, the attending physician may test various bipolar combinations of the leads for defibrillating the heart, using alternatively the patch electrode and/or the defibrillation electrode on the combination lead as the cathode(s) or anode(s) to determine the lowest threshold for defibrillation.

Thus, while it may be necessary to have the patch electrode affixed to or near the exterior surface of the heart (or subcutaneously or subcostally near the heart), preferably if defibrillation can occur by the use of a combination pacing and defibrillation electrode placed in the right ventricle, the necessity for opening the chest cavity and affixing the patch electrode on or near the heart may be avoided.

When utilizing a ventricular pacing lead which also employs a ventricular defibrillation electrode to accomplish pacing, cardioversion or defibrillation, it is important to recognize that preserving atrial—ventricular synchronization, by proper timing of the respective contractions, is very important to prevent the patient from experiencing adverse effects resulting from non-synchronous ventricular contractions. Thus, in addition to providing the necessary ventricular pacing and defibrillation charges, it is extremely beneficial to have a system which can effectively preserve synchronization of the atrial and ventricular contractions by sensing atrial depolarizations, and timing any necessary electrical pacing stimuli to the ventricle in a manner whereby atrial—ventricular synchronization is maintained.

One method of obtaining the additional sensory information required to provide synchronization has been through the utilization of an atrial sensing lead, to provide sensing within the atrial cavity, which provides additional information to the pacemaker. The atrial sensing lead may be passively or actively implanted within the atrial cavity. However, the disadvantages of having a second intravenously implanted lead include the fact that more hardware is implanted, perhaps to the detriment of cardiac function and optimal blood flow, in addition to the potential problems with its placement or implant location, and may result in increased possibility of infections.

Accordingly, it would be very beneficial to provide a pacing system and cardioversion or defibrillation system which utilizes an improved ventricular pacing and defibrillation lead, having the additional capability of being able to sense atrial electrical activity, thereby assisting the preservation of atrial—ventricular synchronization while eliminating the need for an additional atrial sensing lead.

SUMMARY OF THE INVENTION

The present invention details a combination pacing and defibrillation lead for use with an implanted pulse generator which may be a pacemaker or defibrillator or combination thereof. The combination lead can deliver a variety of electrical charges to pace, cardiovert or defibrillate the ventricles of the heart. In addition, the combination lead may include sensing electrodes or other sensors capable of sensing stimulus in the ventricular cavity, including ventricular electrical activity, fluid flow, and pressure, with the use of one or more sensing electrodes. The combination lead may also include ring sensors located so as to be resident in the atrium, to thereby sense atrial depolarization. Finally, an alternative embodiment of the combination lead includes a second electrode located on the combination lead so as to be positioned in the superior vena cava, to allow bipolar defibrillation.

The combination lead allows cardioversion and/or defibrillation stimuli to be provided by a large surface area electrode located just proximal to the tip electrode, so as to be positioned within the ventricle, while also sensing atrial and ventricular activity, to allow the pulse generator to provide ventricular pacing synchronized with atrial depolarizations, as well as cardioversion or defibrillation with a single lead.

BRIEF DESCRIPTION OF THE DRAWINGS

FIG. 1 depicts a pacing and defibrillation combination lead and pulse generator according to the present invention;

FIG. 2 depicts an enlarged view of a portion of the proximal end of the combination lead of FIG. 1;

FIG. 3 depicts an enlarged view of a first connector at the proximal end of the combination lead of FIG. 1;

FIG. 4 depicts an enlarged view of a second connector at the proximal end of the combination lead of FIG. 1;

FIG. 5 depicts the tip electrode at the distal end of the combination lead of FIG. 1;

FIG. 8 depicts an alternative embodiment of a pacing and defibrillation combination lead and pulse generator according to the present invention;

FIG. 9 depicts another alternative embodiment of a combination lead having a vena cava electrode; and FIG. 10 depicts an enlarged partial cross-sectional view of the vena cava electrode of the combination lead of FIG. 9.

DETAILED DESCRIPTION OF THE PREFERRED EMBODIMENT

Figure 6:
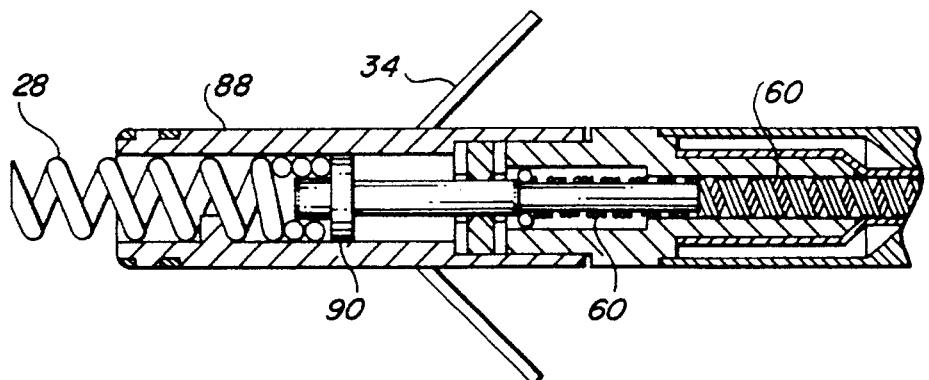
FIG. 6 depicts a view of the tip electrode of FIG. 5 wherein the helical tip electrode is extended.

FIG. 1 depicts a signal processing and pulse generator means, such as a pulse generator 10 which is preferably a pacemaker and defibrillator, and a combination lead 20 providing both pacing and defibrillation electrodes according to the present invention. The combination lead 20 includes a proximal end 22 and a distal end 24. At the proximal end 22, a connector assembly 26 accommodates interconnection with the pulse generator 10. At the distal end 24 of the combination lead 20 is located a tip electrode 28 for sensing electrical activity or delivering pacing stimuli, a distal ring sensor 102 for sensing or delivering pacing stimuli, and a defibrillation electrode 30 for delivering defibrillation or cardioversion stimuli. A lead body 32 interconnects the proximal end 22 and the distal end 24 of the combination lead 20. The combination lead 20 may also include a plurality of tines 34 at the distal end 24, to help secure the positioning of the tip electrode 28 after implant.

The detailed construction of the proximal end 22 of the combination lead 20, including the connector assembly 26, is illustrated in the cross-sectional views of FIGS. 2–4. Initially, it is to be understood that the combination lead 20 of the present invention is designed for use with a variety of pulse generators 10. This is important because while the design of combination lead 20 is unconventional, the capability to function as a pacing lead and as a defibrillation electrode allows substitution for prior designs using multiple leads.

Generally, the pulse generator 10 has a first connector port 12 for receiving a connector of a pacing lead having a pacing electrode at its distal end and a pin-type electrical connector at the proximal end. The first connector port 12 may also include electrical contacts for receiving electrical signals from sensor electrodes on a combination lead, which are interconnected via conductors to electrical contacts on the connector. The electrical contacts are preferably spaced distally of the pin connector for the pacing electrode. The pulse generator 10 may also include a second connector port 16 adapted to receive a connector for a lead extending to a defibrillation electrode. The defibrillation lead generally includes a pin type connector which plugs into a receiving sleeve in the second connector port 16.

In view of the construction of the pulse generator 10, the connector assembly 26 of the combination lead 20 includes a divider boot 38, which allows the combination lead 20 to split into two segments 40 and 42, which terminate at connectors such as first connector 44 and a second connector 46, respectively. The first connector 44 plugs into the first connector port 12, and therefore includes conductors connected to the tip electrode 28 and the distal ring sensor 102. The second connector 46 plugs into the second connector port 16 and therefore includes conductors connected to the defibrillation electrode 30.

The divider boot 38 is shown in the partial cross sectional view of FIG. 2. The divider boot 38 includes an encasement 48 of biocompatible material which is securely affixed about the lead body 32 at one end, and is affixed about both of the segments 40 and 42 at an opposite end. Within the divider boot 38, a defibrillation conductor 52 is illustrated as being wrapped about insulation material 50 which encases the remaining conductors (not shown), at the distal side of the divider boot 38. However, midway along the length of the divider boot 38, the defibrillation conductor 52 diverges, and continues proximally within an insulator 54, to form the segment 42 which terminates at the second connector 46.

The segment 40 extends from the divider boot 38 and terminates at the first connector 44, as depicted in FIG. 3. The first connector 44 includes a connector pin 56 extending into a connector boot 58. The connector pin 56 is securely interconnected to a pacing conductor 60, which terminates at the distal end of the combination lead 20 at the tip electrode 28 (FIG. 1). The connector boot 58 is preferably formed from a biocompatible plastic or elastomeric material such as, for example, silicon, and may include a plurality of sealing rings 62 and a connector grip area 64 extending a short distance from the connector pin 56.

The conductor 60 is encased in an insulation material 66. The conductor 60 is preferably a helically wound coil of multifilar conductors which are braided about a silver core (not shown). The helically wound coil defines a hollow central portion, extending through the center of the helix, which is in open communication with an axial bore 68 in the connector pin 56, allowing for the insertion of a stylet or guidewire (not shown) useful for allowing the proper implanting of the combination lead 20.

A sensor conductor 100 is wound around the insulation material 66. In turn the sensor conductor 100 is encased in the insulation material 50.

The second connector 46 is shown in the detailed cross sectional view of FIG. 4. The second connector 46 includes a connector pin 70 extending into a connector boot 72. The connector pin 70 is securely interconnected to the defibrillation conductor 52. The connector boot 72 is preferably formed from a biocompatible plastic or elastomeric material such as, for example, silicon, and may include a plurality of sealing rings 74 and a connector grip area 76 extending a short distance from the connector pin 70. The defibrillation conductor 52 transitions from being encased in the insulation material 54 into the connector boot 72. The defibrillation conductor 52 is preferably helically wound, and has multifilar conductors which are braided about a silver core (not shown).

FIG. 5 depicts an enlarged cross-sectional view of the distal end 24 of the combination lead 20 (FIG. 1). In FIG. 5, the defibrillation electrode 30 is illustrated as being a coil 80 wrapped about the insulation material 50, through which passes the sensor conductor 100 formed about insulation material 66 which in turn encases the pacing conductor 60. Preferably, the coil 80 of the defibrillation electrode 30 is formed from a platinum-iridium wire. The coil 80 is electrically connected to the defibrillation conductor 52 at the proximal end of the coil 80, via a connector element 84. The connector element 84 preferably interconnects the defibrillation electrode coil 80, to the insulation encasing the defibrillation conductor 52, as well as to the insulation material 50, about which the coil 80 is wrapped. The connector element 84 includes an axial bore 86 through which the remainder of the lead body components pass prior to entering the central portion of the coil 80.

At the distal end 24 of the combination lead 20, the tip electrode 28 is shown retracted into a sleeve 88, which may include the tines 34. The sleeve 88 is preferably formed from a silicone rubber material. The tip electrode 28 is preferably an active fixation corkscrew or helix electrode which is advanceable from the end of the sleeve 88. The tip electrode 28 is affixed to a conductive element 90. The conductive element 90 is also securely affixed to the pacing conductor 60 extending axially through the defibrillation electrode 30, the insulation material 66, the sensor conductor 100, and the insulation material 50 axially fixed within the defibrillation electrode 30, and through the lead body 32 to the first connector 44.

FIG. 6 depicts the tip electrode 28 extended or advanced from the sleeve 88, as it would be following implantation. The tip electrode 28 may be advanced by rotation of the connector pin 56 (FIG. 3) which causes the entire pacing conductor 60 to rotate. Alternatively, a stylet (not shown) may be inserted axially through the combination lead 20 to rotationally advance the tip electrode 28.

Returning to FIG. 5, the sensor conductor 100 may extend the length of the lead body 32, to interconnect a distal ring sensor 102 and an electrical contact 104 in the first connector 44 (FIG. 3). The distal ring sensor 102 is preferably located between the defibrillation electrode 30 and the sleeve 88. The distal ring sensor 102 is spaced from the defibrillation electrode 30 a distance of between one (1) and five (5) centimeters. Following implant of the combination lead 20, the defibrillation electrode 30 will be positioned within the ventricle, as will the distal ring sensor 102.

Figure 7:
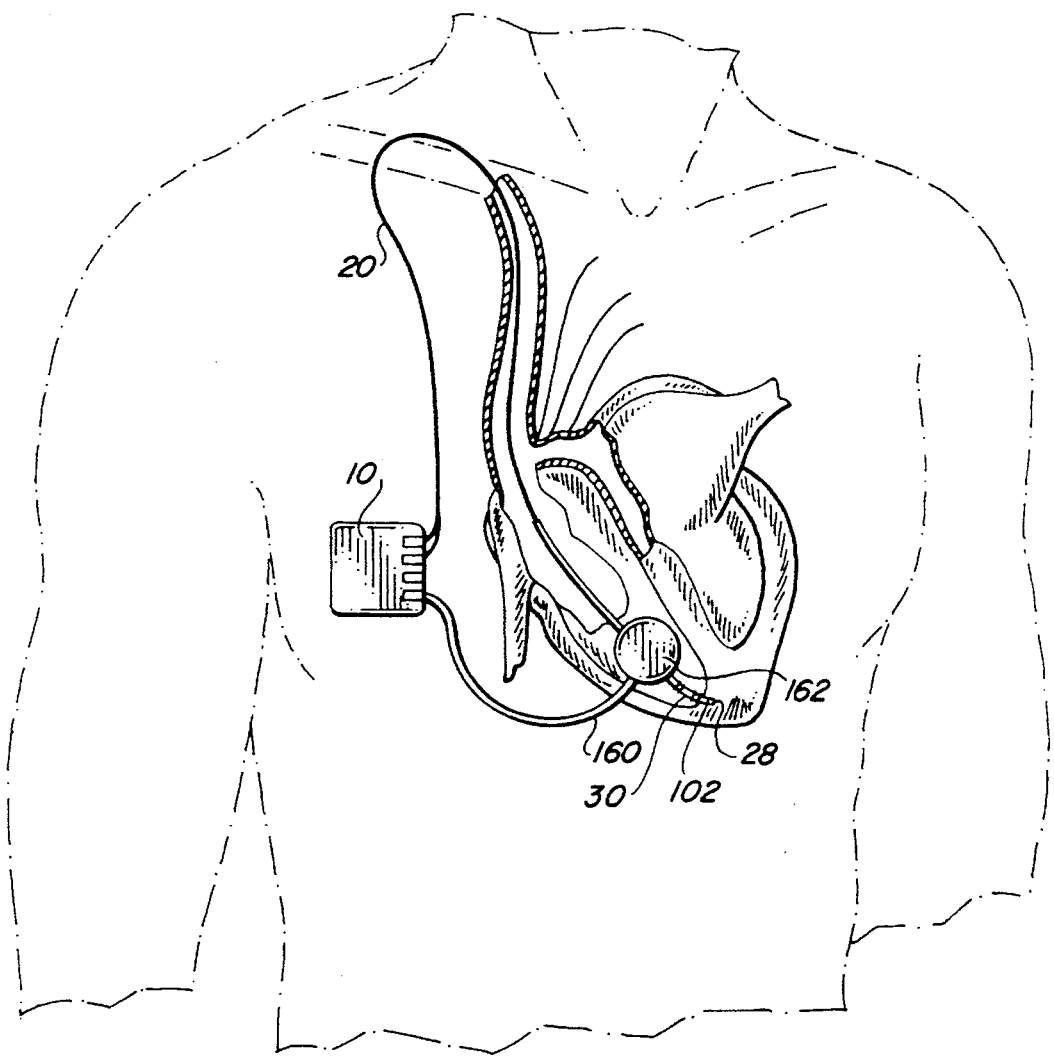
FIG. 7 depicts an implanted pulse generator interconnected via plural leads, including the combination lead of FIG. 1, to a heart.

FIG. 7 depicts a partially cut-away view of an implanted signal processing and pulse generating means such as the pulse generator 10 interconnected via combination lead 20, and a patch electrode lead 160 to a heart. The combination lead 20 is illustrated as being transvenously inserted and extending to the right ventricle. The combination lead 20 includes an electrode assembly which includes the tip electrode 28 in combination with a coil type defibrillation electrode 30. The tip electrode 28 is preferably used with the pulse generator 10 to provide a pacing electrical output to the heart, and also to sense normal pacing electrical activity, in either a unipolar or bipolar arrangement. If a bipolar arrangement is used for pacing, the tip electrode 28 may act as the cathode with the distal ring sensor 102 acting as the anode. Bipolar pacing may also use the tip electrode 28 as the cathode with the defibrillation electrode 30 as the anode.

For defibrillation, the defibrillation electrode 30 of the lead 20 acts as the cathode with the housing of the pulse generator 10 acting as the anode or ground.

As further illustrated in FIG. 7, the patient may also have the patch electrode lead 160, which terminates at a patch electrode 162 affixed to the epicardial surface of the heart, to provide a large electrode useful for acting as either the anode or cathode for bipolar cardioversion or defibrillation. The patch electrode 162 may also be placed near the heart in a subcostal or subcutaneous site. The patch electrode lead 160 is also interconnected to the pulse generator. For a patient which is equipped with both of the leads depicted in FIG. 7, it may be appreciated that cardioversion or defibrillation can be accomplished by a bipolar combination of the defibrillation electrode 30 of combination lead 20 and the patch electrode 162 of patch electrode lead 160. While given a sufficient charge, using either the defibrillation electrode 30 or the patch electrode 162 as a cathode would defibrillate a heart, a key aspect of minimizing the battery drain required for a defibrillation or cardioversion requires that the attending doctor determine which electrode should be the cathode to result in the lowest current threshold required for defibrillation.

FIG. 8 depicts an alternative embodiment of a system having a signal processing and pulse generator means, such as a pulse generator 210 (shown in phantom) which is preferably a pacemaker and defibrillator, and a combination lead 220 according to the present invention. The combination lead 220 includes a proximal end 222 and a distal end 224. At the proximal end 222, a connector assembly 226 accommodates interconnection with the pulse generator 210. At the distal end 224 of the combination lead 220 is a tip electrode 28, tines 34, a defibrillation electrode 30 and optionally a distal ring sensor 102, which are identical to the same elements detailed above with respect to FIGS. 1–5. In addition, a pair of atrial ring sensors 266 and 270 are spaced proximally from the defibrillation electrode 30. A lead body 232 including a plurality of conductors (not shown) extends from the proximal end 222 to the distal end 224 of the combination lead 220.

The combination lead 220 is designed for use with the pulse generator 210 which includes a first connector port 12 and a second connector port 16 as identically described above with respect to elements 12 and 16 of FIG. 1, as well as a third connector port 254. The connector assembly 226 of the combination lead 220 includes a divider boot 238, which splits the combination lead 220 into three segments. The first two segments 240 and 242, terminate at a first connector 44 and a second connector 46, respectively, which are essentially identical to connectors 44 and 46 described above. A third segment 250 extends from divider boot 238 and terminates at a third connector 252. The first connector 44 plugs into the first connector port 12, while the second connector 46 plugs into the second connector port 16, and the third connector 252 plugs into the third connector port 254 of the pulse generator 210. The divider boot 238 includes an encasement 248 of biocompatible material which is securely affixed about the lead body 232 at one end, and is affixed about all three segments 240, 242 and 250 at an opposite end.

The first connector 44 includes a connector pin 56 extending into a connector boot 58. The connector pin 56 is securely interconnected to a pacing conductor which ultimately terminates at the distal end of the lead 220 at the tip electrode 28 as discussed above. The first connector 44 also includes an electrical contact 104 securely interconnected to a sensor conductor which ultimately terminates at distal ring sensor 102. The second connector 46 includes a connector pin 70 extending into a connector boot 72. The connector pin 70 is securely interconnected to a defibrillation conductor which extends through the lead body 232 to the defibrillation electrode 30, also as discussed above.

The construction of the third connector 252 is generally equivalent to that of the first connector 44 discussed above. The third connector 252 thus includes a connector pin 256 extending into a connector boot 258, and also includes a ring connector 260 spaced from connector pin 256. The connector pin 256 and ring connector 260 are securely interconnected to a pair of sensor conductors extending within and through the third segment 250 into the divider boot 238 and through the lead body 232, terminating at the atrial ring sensors 266 and 270, respectively. The atrial ring sensor 266 is positioned proximally from the defibrillation electrode 30 a distance of at least three centimeters, and preferably between about four and six centimeters, with the atrial ring sensor 270 spaced from the atrial ring sensor 266 a distance of between about one and three centimeters, and preferably about one and a half centimeters. This relative spacing of the atrial ring sensors 266 and 270 from the defibrillation electrode 30 results in the ring sensors 266 and 270 being positioned in the atrial cavity upon implantation.

The assembly of FIG. 8 allows sensing of the atrial depolarization, and pacing by stimulating the ventricle with a pacing pulse delivered to the tip electrode 28, with a single combination lead 20. Moreover, by properly programming the pulse generator 210 to the desired delay or interval between when an atrial depolarization is sensed and delivery of a pulse to pace the ventricle, proper atrial—ventricular synchronization can be maintained. Generally, the delay between atrial depolarization and ventricular pacing is about 120 milliseconds for an adult, while a shorter interval may be required for a juvenile or infant.

FIG. 9 depicts another alternative design for a combination lead 278. The combination lead 278 includes the defibrillation electrode 30 proximate a distal ring sensor 102 and a tip electrode 28 at a distal end 224, as well as at least one and preferably a pair of atrial ring sensors 266 and 270 located proximally of the proximal end of the defibrillation electrode 30 as depicted in the embodiment of FIG. 8 detailed above. In addition, the combination lead 278 includes a vena cava electrode 280 spaced proximally of the atrial ring sensors 266 and 270.

The combination lead 278 of FIG. 9 includes a connector assembly at its proximal end. The connector assembly is essentially identical to the connector assembly of FIG. 6. The only modification required of the connector assembly is, providing another electrical contact on the third connector 252. Thus, in addition to the connector pin 256, and ring connector 260, a second ring connector 282 is added to the third connector 252. The ring connector 282 is connected via a vena cava electrode conductor 288 (FIG. 10) within and passing through the third segment 250 and the lead body 232 to the vena cava electrode 280. The remaining electrodes and connectors are essentially interconnected as described above with respect to FIG. 8.

The vena cava electrode 280 is preferably designed as depicted in the enlarged partial cross sectional view of FIG. 10, with a central core sufficiently large to allow pass through of the respective conductors which terminate at the atrial ring sensors 266, 270, defibrillation electrode 30, distal ring sensor 102 and tip electrode 28. The vena cava electrode 280 is illustrated as being a coil 284 wrapped about a sleeve 286. Preferably, the coil 284 is formed from a platinum-iridium material. The sleeve 286 may be formed from a flexible insulation material, so the coil 284 must be coupled to the vena cava electrode conductor 288. Alternatively, the sleeve 286 may be conductive and is also electrically connected to the vena cava electrode conductor 288, which extends into and through the central portion of the sleeve 286. A pair of conductive elements 290, located at the proximal and distal ends of the vena cava electrode 280, are securely affixed to the coil 284 of the vena cava electrode 280, as well as to the sleeve 286. The pair of conductive elements 290, allow interconnection of the vena cava electrode 280, specifically the coil 284, as well as sleeve 286, to the vena cava electrode conductor 288 to provide electrical continuity. The conductive elements 290 include an axial bore through which the remaining conductors and insulators pass.

The vena cava electrode 280 is intended for placement in the superior vena cava upon implant, and to act as an anode in a bipolar defibrillation system using the defibrillation electrode 30 as the cathode. Alternatively, it may be beneficial to defibrillate using the vena cava electrode 280 as the cathode and the defibrillation electrode 30 in the ventricle as the anode.

Following implant of the combination lead 278, the defibrillation electrode 30 will be positioned within the ventricle, the atrial ring sensors 266 and 270 will preferably be positioned within the atrial cavity, and the vena cava electrode 280 will preferably be positioned within the superior vena cava. In order to allow proper placement, the vena cava electrode 280 is preferably located about one and one-half (1.5) centimeters from the atrial ring sensor 270, of between about twelve (12) and sixteen (16) centimeters from the distal end 224 of the combination lead 278. The vena cava electrode 280 may have a surface area in the range of between about 0.5 and 10 square centimeters, with a preferred size of between 3 and 5 square centimeters. Utilizing the combination lead 278, a cardioversion or defibrillation charge applied via the defibrillation electrode 30 will traverse a substantial portion of the heart before reaching the vena cava electrode 280.

For the assembly of FIG. 7, following implantation, the atrial ring sensors 266 and 270 can be redundant sensors which utilize the vena cava electrode 280 in a bipolar manner. Alternatively the atrial ring sensors 266 and 270 are utilized in a bipolar manner, to detect electrical activity in the atrium, particularly atrial depolarizations. For patients having an A-V nodal disease, including first, second or third degree block, depolarization of the atrium may fail to propagate normally to the ventricle, and it therefore fails to initiate the subsequent ventricular depolarization.

In addition to providing atrial sensing, the atrial ring sensors 266 and 270 of FIGS. 8 and 9 may alternately, or in addition, be used as pacing electrodes to deliver electrical stimulus to the atrium and thereby initiate depolarization. Moreover, the electrical stimulus delivered via the atrial ring sensors 266 and 270 may precede a pacing pulse delivered to the tip electrode 28 in the ventricle, to thereby maintain proper atrial-ventricular synchronization.

For any of the foregoing embodiments, the defibrillation electrode 30 may include a coating deposited on the coil 80, the material for the coating being platinum black, carbon, titanium or titanium nitride. The defibrillation electrode 30 has a total surface area in the range of between about two and ten square centimeters, with a preferred size of between four and six square centimeters.

In addition or in the alternative, the tip electrode 28 and/or the defibrillation electrode 30 may be coated with a biocompatible, hypo-inflammatory material. Preferred biocompatible, hypo-inflammatory materials which can be used as coatings include soluble starches such as amylodextrin and amylogen, proteins such as collagen, albumin, and gelatin. These protein materials may be cross-linked with a crosslinking agent such as 1-ethyl-3-(3-dimethylaminopropyl), carbodiimide or hydrochloride. Additionally, ion exchange materials such as polyethylenimine, poly-sodium styrenesulfonates, and sulfonated polytetrafluoroethylene sold under the tradename NAFION by the DuPont Corporation. These materials are preferred because of the ability of the body to resorb them without adverse effect. Polymeric systems including polyethylene oxide or glycol, polypropylene oxide or glycol, polypropylene glycol, polysorbates, poly-vinylalcohol, and copolymers of ethylene oxide/propylene oxide can also be used as the coating material, and can deliver therapeutic agents by co-dissolution due to the inherent solubility of these materials.

The coating material is preferably a mixture of one of the above materials blended with an anti-inflammatory agent such as fluoro-trihydroxy-methyl pregna diene/dione or fluoro-methylprednisolone, sodium phosphate, the sodium salt of methoxy-methyl-naphthalene-acetic-acid, sodium or the sodium salt or forms of dexamethasone sodium phosphate of isobutylphylpropionic acid. The anti-inflammatory agents can constitute between about 1% to 95% by weight of the coating material, preferably however, the anti-inflammatory agents constitute in the range of between 5% and 50% by weight of the coating material.

In view of the foregoing detailed description, the present invention contemplates a method of allowing the delivery of a variety on electrical stimuli to a heart. The method includes programming the combination defibrillation and pacing system having the implantable pulse generator 10 or 210 and the combination pacing lead 20, 220 or 278, implanted so that the tip electrode 28 is positioned within the ventricle abutting or extending into the myocardium of the heart. The atrial ring sensors 266, 270 on the combination lead 220 or 278 allow sensing of the electrical activity of the atrium of the heart, and the pulse generator 210 is programmed to deliver an electrical charge through the combination lead 220 to either the tip electrode 28 or the defibrillation electrode 30. The method specifically contemplates sensing atrial depolarizations utilizing the atrial ring sensors 266, 270 located on the combination lead 220 or 278 proximally spaced from the defibrillation electrode 30, and delivering the electrical stimulus through the tip electrode 28 in the ventricle so as to maintain atrial—ventricular synchronization.

The method also contemplates use of the vena cava electrode 280 on the combination lead 278 in a bipolar defibrillation arrangement whereby either the defibrillation electrode 30 or the vena cava electrode 280 may be used with either or both of the atrial ring sensors 266 and 270 for bipolar sensing.

The foregoing methods may also utilize a patch electrode 162 affixed to the epicardial surface of the heart or placed subcostally or subcutaneously. The patch electrode 162 is connected via a patch lead 160 to the pulse generator 10, and the method utilizes the defibrillation electrode 30 and the patch electrode 162 in cooperation with the pulse generator 10 (or 210) as a bipolar charge delivery system to pace, defibrillate or cardiovert the heart.

It should be evident from the foregoing description that the present invention provides many advantages over leads and pacing or defibrillating systems of the prior art.

Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed

1. An apparatus for ventricular pacing, cardioverting or defibrillating a heart comprising:

an implantable pulse generator;

a lead having a proximal end and a distal end;

a connector assembly attached to the proximal end of said lead, said connector assembly allowing connection of said lead to said pulse generator;

a plurality of conductors within said lead extending from said connector assembly at the proximal end of said lead to the distal end of said lead, said plurality of conductors including at least a pacing conductor, a defibrillation conductor and a sensor conductor and wherein said conductor assembly includes means for electrically interfacing said pacing, defibrillation, and sensor conductors with said implantable pulse generator; and an electrode assembly attached to the distal end of said lead, said electrode assembly including:

a pacing electrode at a distal tip of said electrode assembly, said pacing electrode electrically connected to said pacing conductor;

a defibrillation electrode positioned proximally of said pacing electrode, said defibrillation electrode electrically connected to said defibrillation conductor; and at least one atrial ring sensor positioned proximally from said defibrillation electrode and electrically connected to said sensor conductor.

2. The apparatus of claim 1, wherein said at least one atrial ring sensor is positioned at least three centimeters proximally from said defibrillation electrode.

3. The apparatus of claim 1, wherein the connector assembly at the proximal end of said lead comprises:

a first connector element including a connector electrically attached to said pacing conductor extending to said pacing electrode;

a second connector element having a connector electrically attached to said defibrillation conductor extending to said defibrillation electrode; and a third connector element having at least one connector electrically attached to said sensor conductor extending to said at least one atrial ring sensor.

4. The apparatus, according to claim 3, wherein the lead, further comprises:

a lead body including said plurality of conductors contained within an insulator;

a first segment terminating at said first connector element;

a second segment terminating at said second connector element;

a third segment terminating at said third connector element; and a divider boot merging said first segment, said second segment and said third segment into said lead body.

5. The apparatus of claim 4, wherein said pacing conductor extends through said second segment and said lead body and defines an internal passageway allowing insertion of a stylet for aiding implantation of the lead.

6. The apparatus of claim 1, wherein the at least one atrial ring sensor, further comprises:
   a first atrial ring sensor spaced proximally from the defibrillation electrode a distance of between about four and six centimeters; and
   a second atrial ring sensor spaced proximally from said first atrial ring sensor a distance of between about one and three centimeters.

7. The apparatus of claim 6, wherein the connector assembly and the lead further comprise:
   a first connector element including a connector electrically attached to said pacing conductor;
   a second connector element having a connector electrically attached to said defibrillation conductor;
   a third connector element having a pin connector and a ring connector;
   a first sensor conductor extending from said pin connector of said third connector element to said first atrial ring sensor; and
   a second sensor conductor extending from said ring connector of said third connector element to said second atrial ring sensor.

8. The apparatus of claim 1, further comprising:
   a distal ring sensor positioned between said pacing electrode and said defibrillation electrode; and
   a sensor conductor extending within said lead from said connector assembly to said distal ring sensor.

9. The apparatus of claim 1, further comprising a plurality of tines positioned between said tip electrode and said defibrillation electrode on said electrode assembly.

10. The apparatus of claim 1, further comprising:
    a vena cava electrode spaced proximally from said at least one atrial ring sensor; and
    a vena cava electrode conductor extending within said lead from said connector assembly to said vena cava electrode.

11. The apparatus of claim 10, wherein said vena cava electrode has a total surface area in the range of between about one-half and ten square centimeters.

12. The apparatus of claim 10, further comprising:
    a distal ring sensor positioned between said pacing electrode and said defibrillation electrode; and
    a sensor conductor extending within said lead from said connector assembly to said distal ring sensor.

13. The apparatus of claim 10, wherein the at least one atrial ring sensor further comprises:
    an atrial ring sensor spaced proximally from the defibrillation electrode a distance of at least about four centimeters, said vena cava electrode being spaced proximally from said atrial ring sensor at least about one and a half centimeters.

14. The apparatus of claim 10, wherein the at least one atrial ring sensor further comprises:
    a first atrial ring sensor spaced proximally from the defibrillation electrode a distance of between about four and six centimeters;
    a second atrial ring sensor spaced proximally from said first atrial ring sensor a distance of between about one and three centimeters; and
    said vena cava electrode being spaced proximally from said second atrial ring sensor at least about one and a half centimeters.

15. A combination lead adapted for connection to an implantable pulse generator, said combination lead comprising:
    a lead body having a proximal end and a distal end;
    a plurality of conductors extending through said lead body, said plurality of conductors including at least a pacing conductor, a defibrillation conductor and at least one sensor conductor;
    connector assembly means, attached to said proximal end of said lead body, for providing electrical connectors at the proximal ends of each of said plurality of conductors;
    a pacing electrode at a distal tip of said lead body, said pacing electrode electrically connected to said pacing conductor;
    a defibrillation electrode positioned near the distal end of said lead body, said defibrillation electrode electrically connected to said defibrillation conductor and configured to be passively implanted in the ventricle of a heart; and
    at least one atrial ring sensor spaced at least three centimeters proximally from said defibrillation electrode and electrically connected to a respective sensor conductor of said plurality of conductors extending through said lead body.

16. The apparatus of claim 15, wherein the connector assembly means at the proximal end of said lead includes:
    a first connector element including a connector electrically attached to said pacing conductor;
    a second connector element having a connector electrically attached to said defibrillation conductor; and
    a third connector element having at least one connector electrically attached to said sensor conductor extending to said at least one atrial ring sensor.

17. The apparatus of claim 16, wherein the connector assembly means further comprises:
    a first segment terminating at said first connector element;
    a second segment terminating at said second connector element;
    a third segment terminating at said third connector element; and
    a divider boot merging said first, second and third segments into the proximal end of said lead body.

18. The apparatus of claim 15, wherein the at least one atrial ring sensor, further comprises:
    an atrial ring sensor spaced proximally from the defibrillation electrode a distance of at least about four centimeters.

19. The apparatus of claim 15, wherein the at least one atrial ring sensor further comprises:
    a first atrial ring sensor spaced proximally from the defibrillation electrode a distance of between about four and six centimeters; and
    a second atrial ring sensor spaced proximally from said first atrial ring sensor a distance of between about one and three centimeters.

20. The apparatus of claim 19, wherein the connector assembly means at the proximal end of the combination lead comprises:
    a first connector element including a connector electrically attached to said pacing conductor of said plurality of conductors extending through said lead body;
    a second connector element having a connector electrically attached to said defibrillation conductor of said plurality of conductors extending through said lead body; and
    a third connector element having:

a pin connector attached to a first sensor conductor of said plurality of conductors extending through said lead body to said first atrial ring sensor; and a ring connector attached to a second sensor conductor of said plurality of conductors extending through said lead body to said second atrial ring sensor.

21. The apparatus of claim 15, further comprising:

a distal ring sensor positioned between said pacing electrode and said defibrillation electrode; and a sensor conductor extending within said lead body from said connector assembly means to said distal ring sensor.

22. The apparatus of claim 15, further comprising a plurality of tines positioned between said tip electrode and said defibrillation electrode on said electrode assembly.

23. The apparatus of claim 15, further comprising:

a vena cava electrode spaced proximally from said at least one atrial ring sensor; and a vena cava electrode conductor of said plurality of conductors extending within said lead from said connector assembly means to said vena cava electrode.

24. The apparatus of claim 23, wherein said vena cava electrode has a total surface area in the range of between about one-half and ten square centimeters.

25. The apparatus of claim 23, further comprising:

a distal ring sensor positioned between said pacing electrode and said defibrillation electrode; and a sensor conductor extending within said lead from said connector assembly means to said distal ring sensor.

26. The apparatus of claim 23, wherein the at least one atrial ring sensor further comprises:

a first atrial ring sensor spaced proximally from the defibrillation electrode a distance of between about four and six centimeters;

a second atrial ring sensor spaced proximally from said first atrial ring sensor a distance of between about one and three centimeters; and said vena cava electrode being spaced proximally from said second atrial ring sensor a distance of at least about one and a half centimeters.

27. The apparatus of claim 26, wherein said vena cava electrode has a total surface area in the range of between about three and five square centimeters.

28. The apparatus of claim 26, further comprising:

a distal ring sensor positioned between said pacing electrode and said defibrillation electrode; and a sensor conductor extending within said lead body from said connector assembly means to said distal ring sensor.

29. The apparatus of claim 23, wherein the at least one atrial ring sensor, further comprises:

an atrial ring sensor spaced proximally from the defibrillation electrode a distance of at least about four centimeters, said vena cava electrode being spaced proximally from said atrial ring sensor a distance of at least about one and a half centimeters.

30. An apparatus for pacing, cardioverting or defibrillating a heart, the apparatus including an implantable pulse generator and a combination lead having a lead body extending from a proximal end to a distal end of said combination lead, said combination lead comprising:

a connector assembly at the proximal end allowing interconnection to the implantable pulse generator;

an active fixation pacing electrode located at the distal end of the combination lead;

a defibrillation electrode spaced at least four centimeters from said pacing electrode at the distal end of the combination lead;

sensor means, spaced proximally from said defibrillation electrode, for sensing electrical activity in the atrial cavity and for delivering electrical stimulus; and a vena cava electrode spaced proximally from said sensor means.

31. The apparatus of claim 30, wherein said combination lead, further comprises a plurality of conductors encased within an insulation material and extending from said connector assembly through said lead body, said plurality of conductors each electrically connected at a respective distal end to one of said pacing electrode, defibrillation electrode, sensor means, and vena cava electrode.

32. The apparatus of claim 30, wherein said vena cava electrode includes an electrically conductive coil wrapped about a sleeve.

33. The apparatus of claim 30, wherein said coil of said vena cava electrode is formed from a platinum-iridium wire.

34. The apparatus of claim 30, wherein said atrial sensor means comprises:

an atrial ring sensor spaced proximally from the proximal end of said defibrillation electrode; and at least one sensor conductor interconnected to said atrial ring sensor and extending through said lead body to said connector assembly.

35. The apparatus of claim 34, wherein said atrial ring sensor is spaced from the defibrillation electrode a distance of at least three centimeters.

36. The apparatus of claim 30, wherein said atrial sensor means comprises:

a first atrial ring sensor spaced proximally from the proximal end of said defibrillation electrode;

a second atrial ring sensor spaced proximally from said first atrial ring sensor; and at least two sensor conductors interconnected respectively to one of said first and second ring sensors and extending through said lead body to said connector assembly.

37. A method for monitoring and controlling the electrical activity of a heart, comprising:

programming an implantable pulse generator;

sensing the electrical activity of the heart via a lead connected to said pulse generator, said lead extending to an electrode assembly at a distal end, said electrode assembly having a defibrillation electrode and a pacing electrode positioned within the ventricle of the heart and at least one atrial ring sensor positioned within the atrium of the heart;

determining when an externally generated electrical stimulus is required; and delivering an electrical charge generated by said pulse generator through said lead to the heart.

38. The method, according to claim 37, further comprising:

sensing atrial depolarization; and delivering an electrical stimulus to the ventricle timed so as to maintain atrial—ventricular synchronization based on the sensed atrial depolarization.

39. The method, according to claim 38, further comprising sensing atrial electrical activity utilizing said at least one atrial ring sensor, said at least one atrial ring sensor located on said lead proximally spaced at least three centimeters from said defibrillation electrode.

40. The method, according to claim 37, further comprising:

operating said pacing electrode and said defibrillation electrode of said electrode assembly in combination with said pulse generator to define a bipolar electrical charge delivery system capable of bipolar pacing.

41. The method, according to claim 37, further comprising:

providing a vena cava electrode on said lead, said vena cava electrode located proximally from said at least one atrial ring sensor as well as said defibrillation electrode; and operating said defibrillation electrode and said vena cava electrode in cooperation with said pulse generator as a bipolar charge delivery system to defibrillate or cardiovert the heart.

42. The method, according to claim 37, further comprising:

providing a patch lead having a patch electrode affixable proximate the epicardial surface of said heart;

interconnecting said patch lead to said pulse generator; and operating said defibrillation electrode and said patch electrode in cooperation with said pulse generator as a bipolar charge delivery system to defibrillate or cardiovert the heart.

\* \* \* \* \*